(12) United States Patent
Champagne (10) Patent No.: US 8,597,337 B2
(45) Date of Patent: Dec. 3, 2013

(54) JOINT FUSION DEVICE

(76) Inventor: Lloyd P. Champagne, Paradise Valley, AZ (US)

(*) Notice: Subject to any disclaimer, the term of this patent is extended or adjusted under 35 U.S.C. 154(b) by 718 days.

(21) Appl. No.: 12/372,712

(22) Filed: Feb. 17, 2009

(65) Prior Publication Data

US 2009/0210016 A1    Aug. 20, 2009

Related U.S. Application Data

(60) Provisional application No. 61/028,791, filed on Feb. 14, 2008.

(51) Int. Cl.
*A61B 17/04* (2006.01)
*A61B 17/86* (2006.01)
*A61F 2/08* (2006.01)

(52) U.S. Cl.
USPC ......... 606/309; 606/315; 606/316; 623/21.15

(58) Field of Classification Search
USPC ......... 606/62, 63, 315, 323, 329, 78, 316, 76, 606/77; 623/21.11, 21.15, 21.19
See application file for complete search history.

(56) References Cited

U.S. PATENT DOCUMENTS

| | | | |
|---|---|---|---|
| 5,312,255 A | 5/1994 | Bauer | |
| 6,475,242 B1 * | 11/2002 | Bramlet | 623/21.11 |
| 6,607,530 B1 * | 8/2003 | Carl et al. | 606/914 |
| 7,041,106 B1 * | 5/2006 | Carver et al. | 606/309 |
| 2002/0198527 A1 * | 12/2002 | Muckter | 606/73 |
| 2007/0282342 A1 | 12/2007 | Niederberger et al. | |
| 2009/0062868 A1 | 3/2009 | Casutt | |

FOREIGN PATENT DOCUMENTS

| | | |
|---|---|---|
| WO | WO9733537 A1 | 9/1997 |
| WO | 2004093700 A1 | 4/2004 |
| WO | 2005092226 A1 | 10/2005 |
| WO | 2006105935 A1 | 12/2006 |
| WO | 2007109140 A1 | 9/2007 |

* cited by examiner

*Primary Examiner* — Andrew Yang
(74) *Attorney, Agent, or Firm* — Snell & Wilmer LLP (57) ABSTRACT

A device and method are disclosed for the fusion of joints (particularly finger joints or toe joints) in a bent (or angled) position. In certain embodiments, a device for the fusion of joints preferably allows for one or more of various angled positions, and the particular angle may differ for different joints. The device is preferably a bendable implant device for fusing together bones or a joint.

29 Claims, 10 Drawing Sheets

JOINT FUSION DEVICE

CROSS REFERENCE TO RELATED APPLICATIONS

This application is related to and claims priority to U.S. Provisional Application No. 61/028,791, filed Feb. 14, 2008, entitled "Joint Fusion Device."

DESCRIPTION OF THE INVENTION

1. Field of the Invention

The present invention relates to a device or method for the fusion of joints in a predetermined position.

2. Background of the Invention

The palm of the hand is made up of bones called metacarpals, and a metacarpal connects each finger and thumb to the hand. Each finger and thumb is formed of bones called phalanges. The connection of the phalanges to the metacarpals is called a "knuckle" joint or metacarpophalangeal joint (MCP joint), and acts like a hinge when the fingers or thumb are bent.

In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint.

The joints are covered on the ends with articular cartilage. Damage to the joints may occur as a result of arthritis, a sprain or fracture, and wherein the damage either directly or indirectly affects the articular cartilage. Typically, the joint does not line up the same after the injury and causes unusual wear on the articular cartilage, eventually damaging the articular surface and causing pain and loss of mobility.

Typical methods of surgically treating a damaged joint include artificial joint replacement or fusion. Fusion (arthrodesis) is used to enable bones that make up a joint grow together into one solid bone. Fusions are commonly used in the PIP or the DIP joints in the fingers because it is easier than replacing the joint and is an acceptable alternative to replacement in many cases.

Existing methods of fusion are inadequate, such as (a) k-wire fusion, (b) or inserting a screw through the tip of the finger and through the joint to be fused because the joint is typically fused straight (i.e., without a bend in it), which is not a natural position for the joint of a finger during normal use. Herbert and Accutrack screws and their variants have been used, but by using these the joint (DIP joint) and end of the finger are fused in a straight position, which is unnatural since the joint is normally bent during use. DIP fusions with angles can be performed but the process is technically demanding, so it is rarely performed. Additionally, the ability to angle the joint is limited and the bone purchase is poor.

Other techniques such as pin and tension band or cerclage wire do not adequately solve the problem of easily fusing a finger joint in a bent position.

SUMMARY OF THE INVENTION

It is to be understood that the descriptions of this invention herein are exemplary and explanatory only and are not restrictive of the invention as claimed.

A device for fusing joints comprises: (1) a first end, (2) a second end, (3) a middle bendable section, (4) a section between the first end and the middle bendable section that can adhere to the interior of a joint to be fused (this section is preferably threaded) wherein the outer surface between the first end and the middle bendable section preferably includes a first threaded section (or other structure for securing the section to bone), and (5) a section between the second end and the bendable middle section that can adhere to the interior of a joint to be fused (this section is preferably threaded) wherein the outer surface between the second end and the middle bendable section includes a second threaded section. The device may further include a channel or cannula therethrough to receive a support and guide structure, such as a Kirschner wire (or "K-wire").

In an alternative embodiment, removing the support structure initiates the movement of the device from a straight position to an angled position, because the device was formed pre-bent and straightens out as it is placed over the K-pin or other structure received in the cannula. In this embodiment, inserting the support structure into the cannula initiates the movement of the device from an angled position to an approximately straight or unbent position. The support structure may be removed without altering the anchoring of the device.

In one embodiment, the middle, bendable section can be bent at an angle of between 1 and 20 degrees. Alternatively, the middle bendable section can be bent at an angle of between 1 and 45 degrees. In yet another embodiment, the middle bendable section can be bent at an angle of between 1 and 60 degrees. The device may be between ½" and 2" long. Alternatively, it may be between ¾" and 1¾" long. In one embodiment, the device is between 1 mm to 5 mm in diameter at its thickest point. Alternatively, it may be about 3 mm in diameter at its thickest point.

If threads are used, the first threaded section may have a higher or otherwise different thread pitch than the second threaded section, or the first threaded section may have same thread type and pitch as the second threaded section. The device may include a self-tapping feature at the first end and a head at the second end adapted to receive an end of a driving tool, such as a screwdriver.

The middle bendable section may be made of the same material as the rest of the device or at least part of the middle bendable section may comprise a different material than the rest of the device. In one embodiment, at least part of the first end, second end, and middle bendable section are comprised of nitinol.

In one embodiment, the middle bendable section is designed to bend in one direction. In another embodiment, the middle bendable section is designed to bend in more than one direction. The middle bendable section may comprise between 20% to 75% of the device length. Alternatively, the middle bendable section may comprise between 25% to 50% of the device length. In one embodiment, at least a portion of the middle bendable section has a diameter that is less than a diameter of one or more of: the diameter of part of the first end and the diameter of part of the second end. Alternatively, the middle bendable section may have the same diameter as the first section and/or second section. The device may include an orientation marker for aligning the device when placed inside a joint to enable a health care professional to know the device is in position to properly bend the finger or toe.

In one embodiment, between 2 and 30 lbs. of force is required to bend the middle bendable section once the device is implanted into a patient. In another embodiment, between 2 and 10 lbs. of force is required to bend the bendable section once the device is implanted into a patient.

The invention also includes a method of fusing a joint, including: (1) joining a first phalange to a first end of a device, and (2) joining a second end of the device to an adjacent phalange. The device used comprises: a shaft having a surface and comprising: the first end, the second end, a channel disposed inside the first end coupled to the second end configured to receive a support structure, and a middle bendable section. The surface between the first end and the middle bendable section may include a first threaded section, and the surface between the second end and the middle bendable section may include a second threaded section.

The method includes (1) bending the device to a determined angle, (2) inserting a support structure into the first end of the channel resulting in a reduction of the determined angle, (3) inserting the first end of the device into a bore dimensioned to accept the first end of the device, (4) orienting the device into a predetermined orientation, and (5) removing the support structure resulting in the device bending to the determined angle. In one embodiment, the reduction of the determined angle is approximately unbent. A cover may be coupled on the second end of the channel after the support structure is removed. In one embodiment, the bore for the device is dimensioned through a first phalange and the proximal end of an adjacent phalange.

BRIEF DESCRIPTION OF THE DRAWINGS

The present invention is further described in conjunction with the drawing figures.

DESCRIPTION OF PREFERRED
EMBODIMENTS OF THE INVENTION

A device or method according to the invention allows for the fusion of joints in the finger (particularly the DIP joint) in a bent (or angled) position, which is more natural when using the hand. In certain embodiments, a device for the fusion of small hand joints preferably allows for one or more of various angled positions, and the particular angle may differ for different joints. The device is preferably a bendable screw implant for fusing together bones or a joint, and most preferably is used for bones or a joint in a finger or toe.

Figure 1:
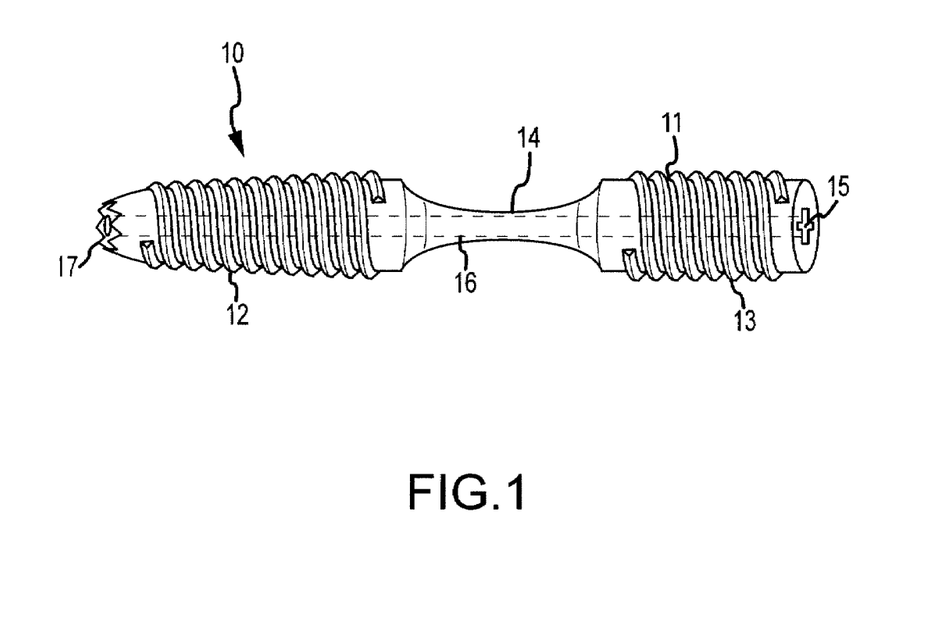
FIG. 1 is a perspective view of one embodiment according to the present invention.

With reference to FIG. 1, in one embodiment, the device is a screw 10 that has a substantially cylindrical and elongated central body 11, threaded surfaces 12, 13 approaching each end, and a bendable region 14 between threaded surfaces 12, 13. Screw 10 may have a cannula 16 as shown, which facilitates its use over a guide wire. In one embodiment, end 15 is adapted to receive a Phillips head screw driver, but any suitable adaptation is possible, such as a slotted, Torx, Pozidriv, Robertson, tri-wing, Torq-Set, Spanner Head, Triple Square, or hex configuration, or any other configuration capable of pushing or screwing the device into the body, particularly into the end of a finger or toe, in order to fuse a joint. In certain embodiments, an end of the device may be adapted to be self tapping by utilizing sharp ridges 17, but it is not limited thereto.

Figure 2:
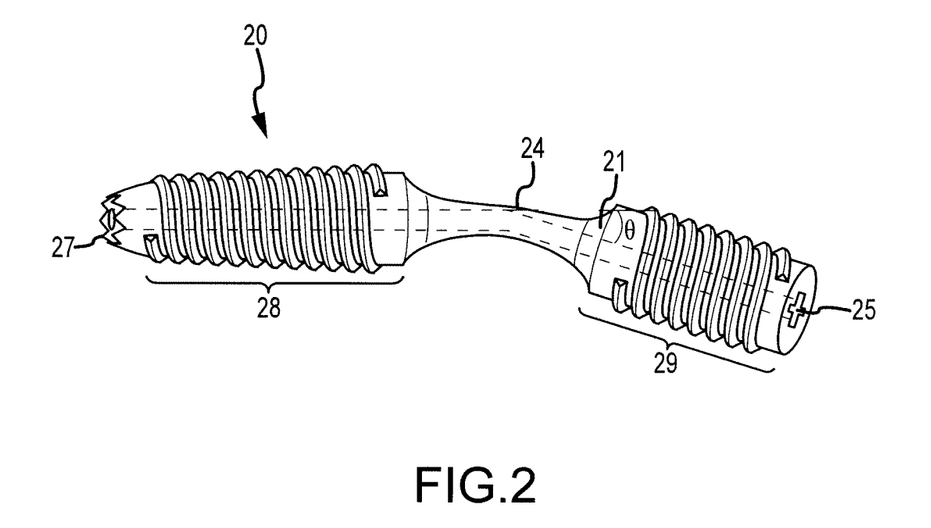
FIG. 2 is another perspective view of an angled embodiment according to the present invention.

As illustrated in FIG. 2, a device, which is shown as screw 20 (which in this case has the same configuration as screw 10) has a bendable region 24 of middle section 14. Bendable region 24 allows screw 20 to be configured for different joints by changing the angle between ends 25, 27 after the device is inserted into the body (preferably into the end of a finger). Angle 21 is formed after the device is inserted into the joint and the angle is determined according to any desired fusion position. Angle 21 could be any angle between about 5 and 70 degrees and most preferably between about 15 and 45 degrees.

Figure 3:
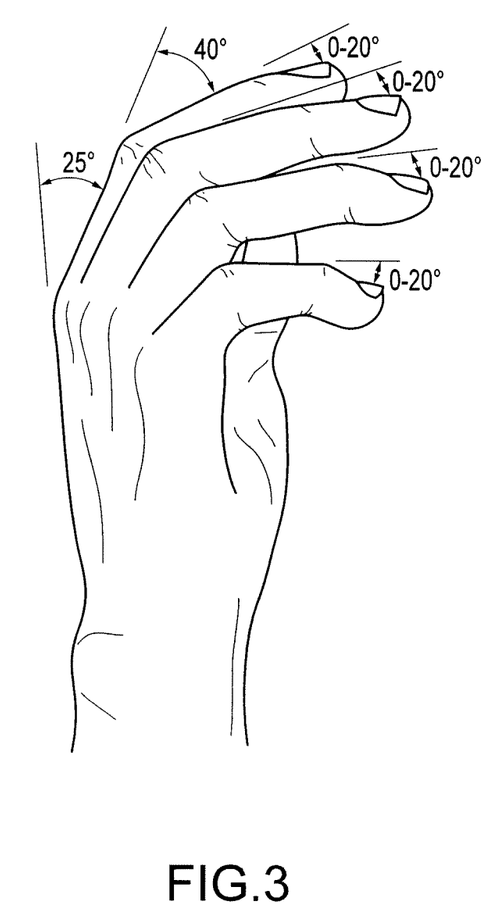
FIG. 3 illustrates optional angles for setting the different small joints in a typical hand utilizing a device according to embodiments of the invention.

FIG. 3 illustrates preferred, optimal angles for setting the different small joints in a typical hand utilizing a device according to the invention. However, different hands and different people may require different fusion angles, which can be accommodated by the invention. In some embodiments, the flexed position for the PIP joints is about 40-55 degrees, the DIP joints may vary from about 0-20 degrees, the MCP joints may vary from about 25-40 degrees, and the IP joint is typically about 20 degrees. In preferred embodiments, the angle of the device when bent is not a sharp angle, but is curved (so the bend in the bendable region, such as region 14 or region 24, is radiused or curved).

The bendable region 14 or 24 may be constructed of the same material as the rest of screw 10 or 20, and is bendable because of a reduced diameter or cross-section. In another embodiment, bendable region 14 or 24 has a different composition form the other areas of screw 10 or 20 that is more malleable, thus allowing the bendable region to bend. In preferred embodiments, bendable region 14 or 24 is bendable by a surgeon or other health-care professional after screw 10 or 20 has been inserted into the joint, and can be bent by applying between about 2 lbs. to 30 lbs. of force, and most preferably between about 2 lbs. and 10 lbs. of force. Once inserted and bent, the device is rigid enough so that ordinary use by the patient will not cause the middle bendable region to further bend or straighten out.

In some embodiments, the device material is one or more of titanium and stainless steel, but the device is not limited to these materials. The device may be comprised of any material(s) capable of fusing a finger joint, allowing the surgeon to bend the device after being inserted into a joint, and rigid enough to prevent a patient from straightening it during ordinary use.

The length of the device, such as screw 20, depends on the size of the joint and phalanges, but is preferably between ½" and 2" and most preferably between ¾" and 1½". In many embodiments, the maximum diameter of the device is the outer diameter of the highest thread, which may be between 1 mm and 5 mm, and most preferably about 3 mm. A device according to the invention may have the same diameter along its entire length, may have taper from one end to another or may have different sections with different diameters.

First threaded section 28 should be long enough and of sufficient diameter such that when inserted into a bore in a phalange, the threads grip the bone and do not allow screw 20 to twist without applying torque to end 25. Second threaded section 29 should be long enough and of sufficient diameter such that when inserted into a bore of an adjacent phalange, the threads grip the bone and do not allow screw 20 to twist. The diameter of first section 28 may taper down from bendable section 24 to first end 27. In some embodiments, the diameter of first section 28 is constant. The diameter of second section 29 may taper down from bendable section 24 to second end 25. In some embodiments, the diameter of second section 29 is constant. In further embodiments, the diameter of first section 28 is different from the diameter of second section 29.

A k-wire or pin is a sterilized, smooth stainless steel pin used in orthopaedics and other types of medical applications. It comes in different sizes as needed and provide structure support, and one size has a diameter of about 0.040".

The bored hole into which the screw fits has an internal diameter that is preferably the size of the screw minus the pitch of the thread. The pitch of first section 28 may be high or low and the pitch of second section 29 may be high or low. In one embodiment, the pitch of first section 28 is high and the pitch of second section 29 is low. Sections 28 and 29 may have the same or different pitches.

Figure 4:
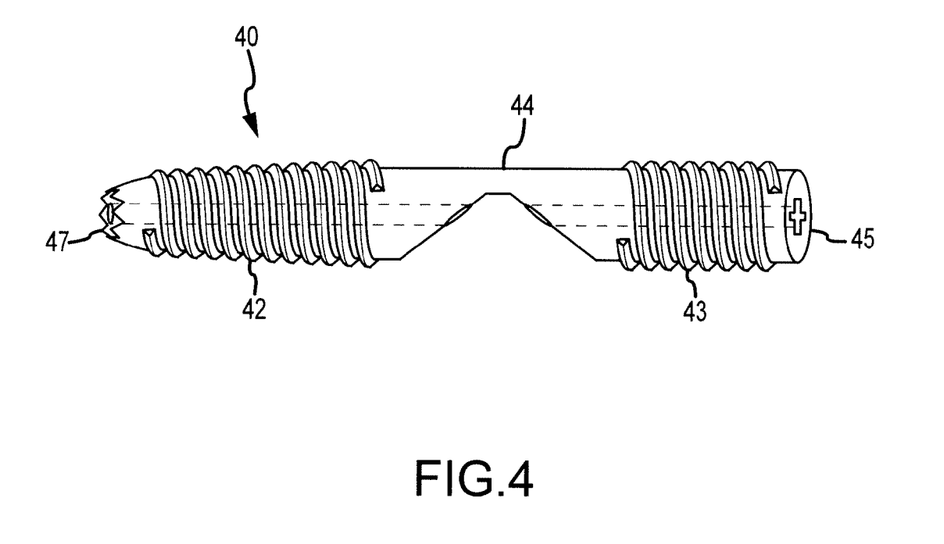
FIG. 4 is another perspective view of an angled embodiment according to the present invention.

As illustrated in FIG. 4, in some embodiments the bendable section, such as section 44, has a reduced diameter and is formed so that just one side of section 44 tapers or has reduced material. In one embodiment, bendable section 44 is created by removing material from, or not including material into, screw 40 such that a "V" shape is created in bendable section 44. Alternatively, a reduced diameter (if utilized) of bendable section 44 may be formed in any suitable manner. As previously mentioned, the bendable section may instead be comprised of a malleable material and not have a reduced diameter.

Figure 5A:
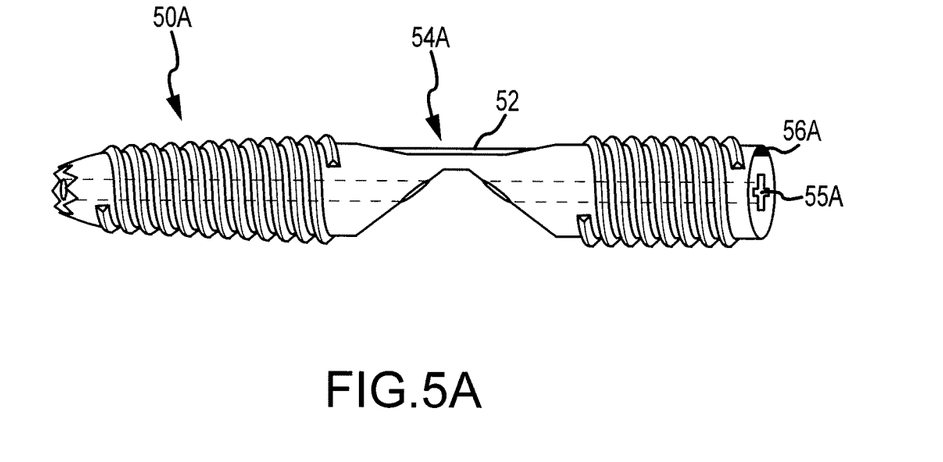
FIGS. 5A and 5B depicts embodiments of the device of FIG. 4 in operation.
Figure 5B:
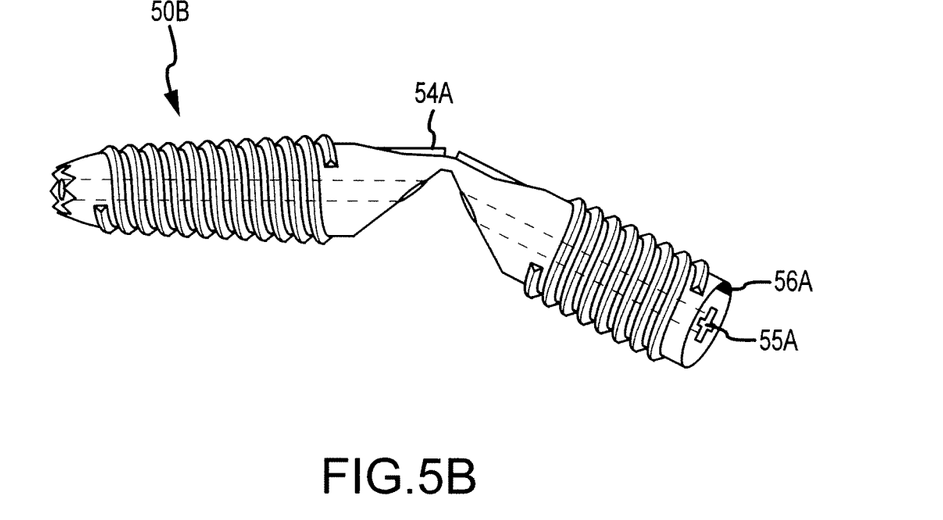

In several embodiments, and as illustrated in FIGS. 5A, B, the bendable section, such as section 44, may be prevented from bending by using a bend-back stopper 54A. In one embodiment, the bend back stopper is applied to the top surface of screw 50A where a bend is desired. Bend-back stopper 54A may be constructed of a material different from screw 50A, or may be a similar material with an optional kerf 52, thereby allowing easy bending. Upon the application of force by a surgeon, bend-back stopper 54A opens at the bend location, thereby allowing the screw to bend.

One or more orientation marks may be incorporated into the screws of the present invention. In some embodiments, as illustrated in FIGS. 5A, B, an orientation markers 56A is placed at the second end of screw 50A allowing the surgeon to know when the bending section is in the proper position relative to the first phalange and the adjacent phalange. An orientation marker is particularly useful (but not required) if the bendable middle section is designed to bend in one direction.

In one embodiment, orientation marker 56A may be an indentation stamp in the second end 55A of screw 50A or may be cast into screw end 55A or may be a mark made with a surgical marker.

Figure 6A:
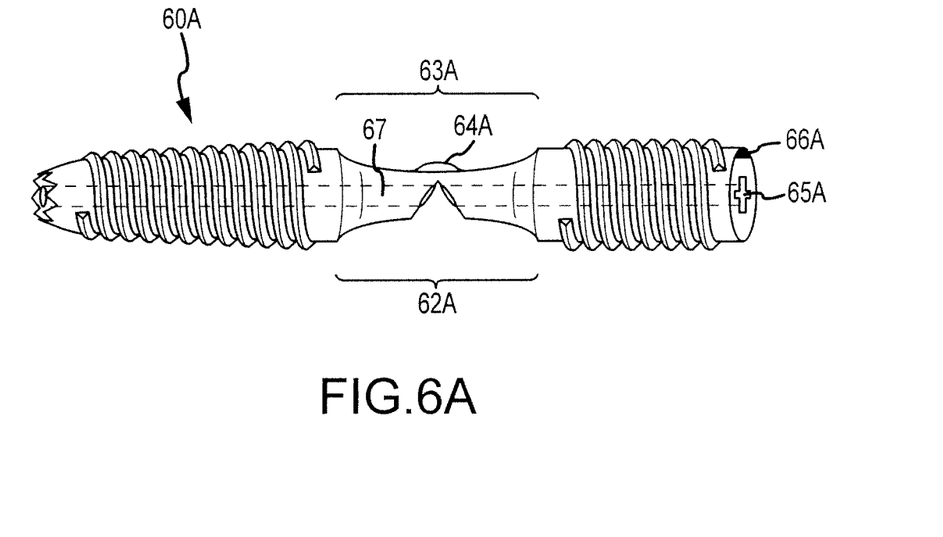
FIGS. 6A and 6B depicts embodiments of the device of FIG. 1 in operation.
Figure 6B:
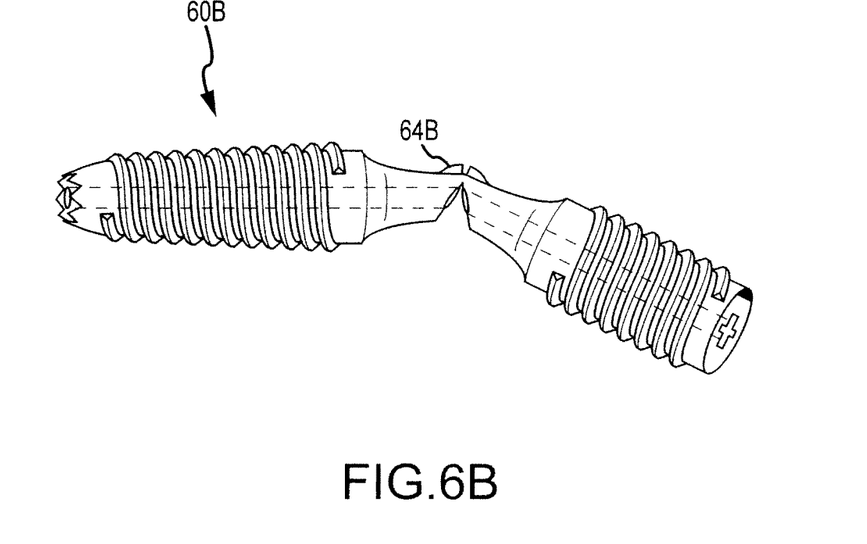

An additional embodiment of a device according to the invention is screw 60A illustrated in FIGS. 6A, B. In some embodiments, the bendable section (shown as 62A and 63A) is a reduced diameter section with the bottom bendable section 62A cutting into the cannula 67. Top bendable section 63A, which may be identified by orientation mark 66A at second end 65A, may also include a bend-back stopper 64A. Upon bending screw 60A, the bend-back stopper is separated 64B, resulting in bent screw 60B.

Figure 7:
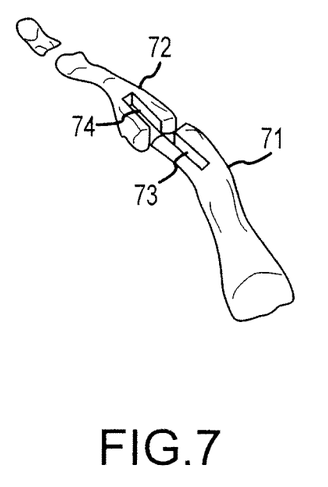
FIG. 7 illustrates one example of a PIP joint.

The invention also includes a method of fusing a joint using the devices disclosed herein. FIG. 7 illustrates a PIP joint, although the procedure would be similar for a DIP or MCP joint. In an embodiment as illustrated in FIG. 7, a first phalange 71 is joined to a second adjacent phalange 72 using one of the devices disclosed above. In certain embodiments, a bore 73 is provided in the distal end of a first phalange 71 and a bore 74 is provided in the proximal end of the adjacent phalange 72. A device (not shown) is preferably a screw with a first threaded end, a central bendable region, and a second threaded end is inserted into bore 73 of first phalange 71 and into bore 74 of adjacent phalange 72 using a screwdriver. Before inserting the screw into the bore of the first phalange, the bendable region may initially have zero bend, or may be pre-bent to a desired fusion angle as discussed above and shown in FIG. 3. In some embodiments, the bendable region may be bent to a desired angle after one end has been inserted into the bore of the first phalange. In other embodiments, the bendable region is bent after the second end has been placed into the bore of the adjacent phalange. In yet another embodiment, the bendable region is further bent at a later time, after the screw has been inserted.

Figure 8A:
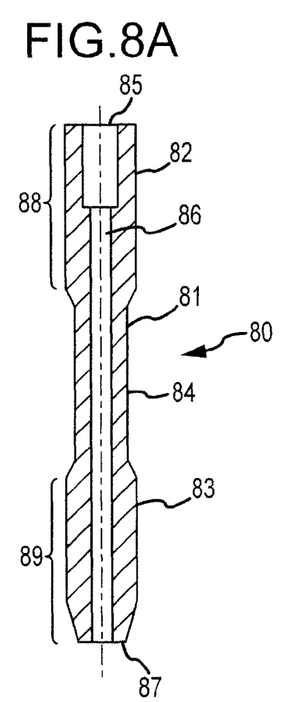
FIGS. 8A-8D are views of an embodiment according to the present invention.
Figure 8B:
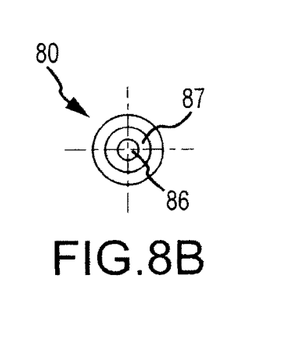
Figure 8C:
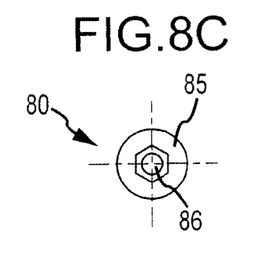
Figure 8D:
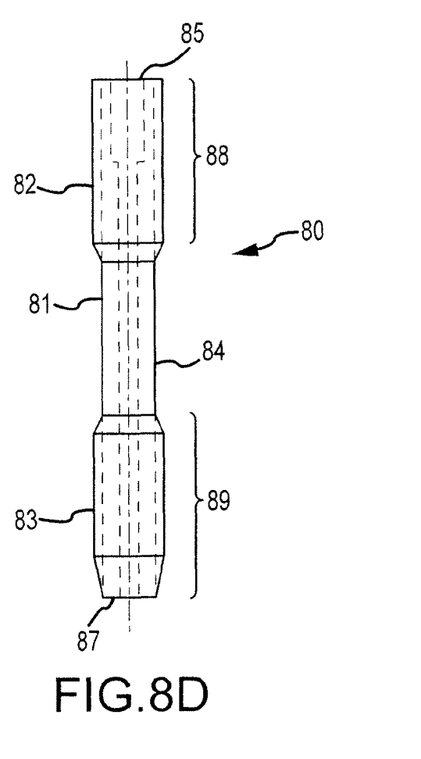
Figure 9A:
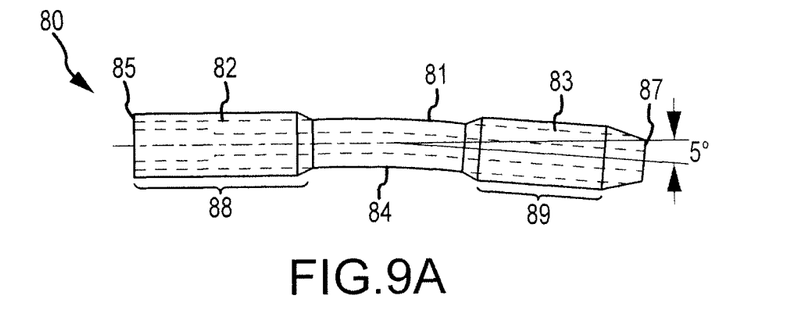
FIGS. 9A-9C are angled configurations of the embodiment shown in FIGS. 8A-8D according to the present invention.
Figure 9B:
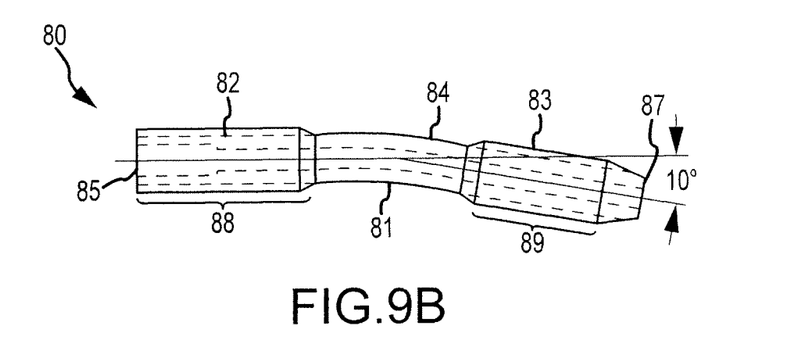
Figure 9C:
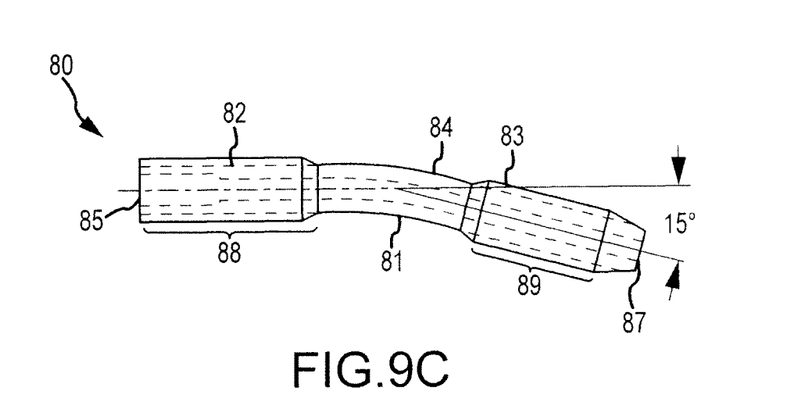

In another embodiment for use with any of the previously-described joints (particularly joints in the fingers and toes), as shown in FIGS. 8A-8D, fusion device 80 has a substantially cylindrical and elongated central body 81, threaded surface 82, 83 near each end, and a bendable region 84 between threaded surfaces 82, 83. Screw 80 may have a channel (or cannula) 86 as shown, which may receive a support structure, such as a K-pin. The support structure may be any material strong enough to initiate the device to retract to a substantially unbent position or configuration. Channel 86 may be any suitable diameter to receive a support structure, but its diameter is preferably about 1.3 mm. Channel 86 may run the entire length of the device or it may run a portion the length of the device. Channel 86 may be a slightly larger diameter near the second end of the device (as shown in FIG. 8A) to accommodate gripping by an insertion and removal tool. In another embodiment (not shown), channel 86 may be capped at one end. This cap may run any desired length into the first end 87 and/or second end 85 of the device, and may further be integral to the device.

In one embodiment, end 85 is adapted to receive a Phillips head screw driver, but any suitable adaptation is possible, such as a slotted, Torx, Pozidriv, Robertson, tri-wing, Torq-Set, Spanner Head, Triple Square, or hex configuration, or any other configuration capable of pushing or screwing the device into the body, particularly into the end of a finger, in order to fuse a joint. In certain embodiments, an end of the device may be adapted to be self tapping by utilizing sharp ridges 87, but it is not limited thereto. As in previous embodiments, the bendable region 84 of screw 80 may be set to any desired angle such as between about 5 and 70 degrees and most preferably between about 5 and 45 degrees.

In some embodiments, the material comprising fusion device 80 is one or more of titanium, nitinol, (nickel titanium) CuSn, InTi, TiNi, and MnCu and stainless steel, but the device is not limited to these materials.

Nitinol is a shape memory metal. A reversible, solid phase transformation known as martensitic transformation is the force behind shape memory alloys. The alloy material forms a crystal structure, which is capable of undergoing a change from one form of crystal structure to another. Temperature change or/and loading may initiate this transformation. A Kirschner pin is then inserted in the first end 85 of the of the device 80. The device 80 may be comprised of any material(s) capable of fusing a finger joint, allowing the surgeon to bend the device 80 after (and/or prior to) being inserted into a joint, and rigid enough to prevent a patient from straightening it during ordinary use. Each section may be made of different materials or they may be made of the same materials. As previously described one or more orientation marks may be incorporated into the screw of the present invention.

As previously described, screw 80 further includes a first threaded section 83 which should be long enough and of sufficient diameter such that when inserted into a bore in a phalange, the threads grip the bone and do not allow screw 80 to twist without applying torque to end 85. Second threaded section 82 should be long enough and of sufficient diameter such that when inserted into a bore of an adjacent phalange, the threads grip the bone and do not allow screw 80 to twist. These threaded sections may be made from nitinol or from a suitable different material such as stainless steel.

As show in FIGS. 8A-8D, and 9A-9C, screw 80 according to the invention may have the same diameter along its entire length, may have taper from one end to another or may have different sections with different diameters. The lead end or first end 87 of screw 80 may be shaped to assist its insertion into the phalange bore. The diameter of second section 88 may taper down from bendable section 84 to second end 85. In some embodiments, the diameter of second section 88 is constant. The diameter of first section 89 may taper down from bendable section 84 to first end 87. In some embodiments, the diameter of first section 89 is constant. Alternatively, as shown in FIGS. 8A-8D and 9A-9C, the diameter of section 89 may taper down at both ends and the diameter of second section 88 may taper down approaching bendable section 84. In further embodiments, the diameter of second section 88 is different from the diameter of first section 89.

Figure 10A:
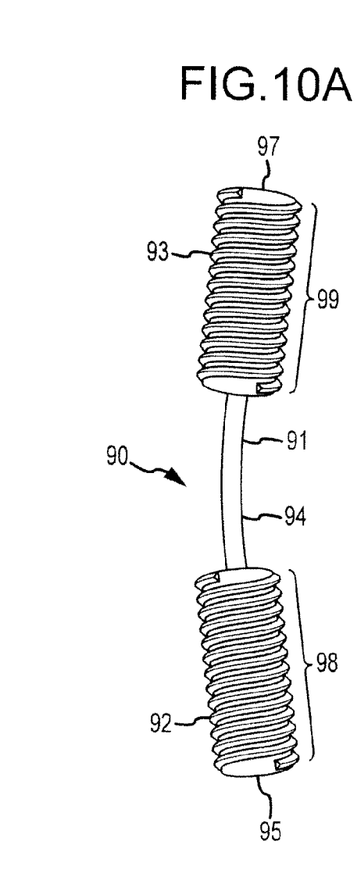
FIGS. 10A-10C are embodiments of the preset invention showing different predetermined angled configurations.
Figure 10B:
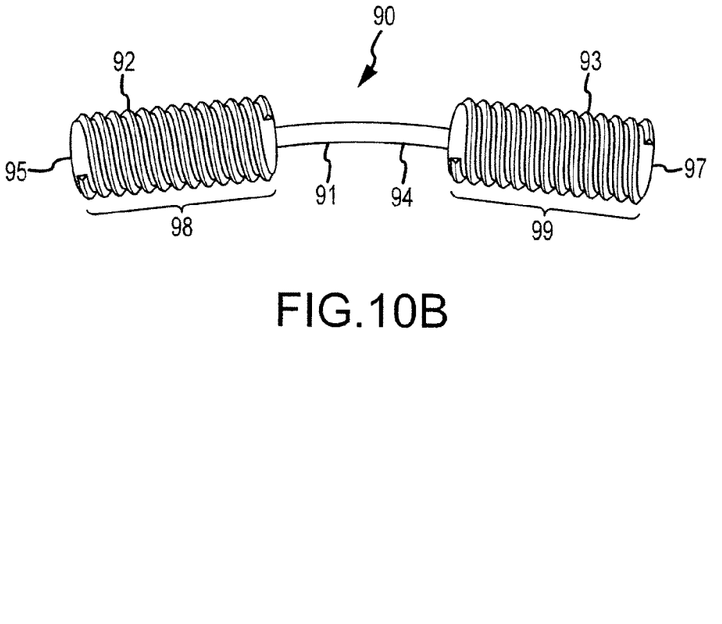
Figure 10C:
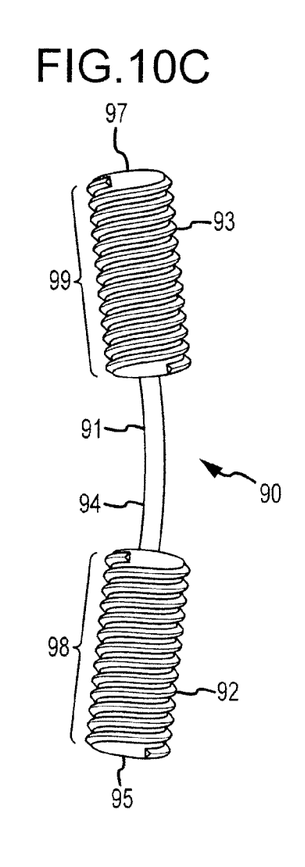

FIGS. 10A-10C are preferred embodiments of the present invention showing different predetermined angles. A flexible tube 90 is depicted with substantially rigid collars 92, 93 coupled to either end of the tube in any suitable manner. For instance, these collars 92, 93 may be coupled to the tube using an adhesive, soldering, and/or machined from nitinol and/or integral to the tube. In this embodiment the rigid collar may be made from any suitable rigid material such as steel and/or stainless steel, hard plastic, titanium, and ninitol. The collars may be threaded 92, 93 to help secure the device in the bore dimensioned to accept the first end 97 of the device 90.

Alternatively, the collars may be barbed or formed with a deformable collar piece that is capable of holding the device in place through friction and/or pressure fit. The device 90 should remain in place once inserted for a suitable time so that the desired bones may fuse.

In the present embodiment depicted in FIGS. 10A-10C, the tube is a nitinol tube, however, any suitable material may be utilized such as titanium, CuSn, InTi, TiNi, and MnCu, other bimetals and/or stainless steel, but the device is not limited to these materials. The device 90 may be a three piece structure, or it may be a two piece or one piece structure. For instance, the device 90 may be made from many materials or as few as one material. The device 90 may be a nitinol tube with a larger collared section on either end or the tube may be approximately the same diameter as one or both of the collared ends.

As previously described, screw 90 further includes a first threaded section 93 which should be long enough and of sufficient diameter such that when inserted into a bore in a phalange, the threads grip the bone and do not allow screw 90 to twist without applying torque to end 95. Second threaded section 92 should be long enough and of sufficient diameter such that when inserted into a bore of an adjacent phalange, the threads grip the bone and do not allow screw 90 to twist. As previously described, the threads may be made from any suitable material.

Screw 90 according to the invention may have the same diameter along its entire length, may have taper from one end to another or may have different sections with different diameters. The lead end or first end 97 of screw 90 may be shaped to assist its insertion into the phalange bore. The diameter of second section 98 may taper down from bendable section 94 to second end 95. In some embodiments, the diameter of second section 98 is constant. The diameter of first section 99 may taper down from bendable section 94 to first end 97. In some embodiments, the diameter of first section 99 is constant. Alternatively, the diameter of section 99 may taper down at both ends and the diameter of second section 98 may taper down approaching bendable section 94. In further embodiments, the diameter of second section 98 is different from the diameter of first section 99.

Once the predetermined angle of the device is determined by the desired angle of bone fuse, the device is set to the predetermined angle. The predetermined angel may be zero. As depicted in FIGS. 9A-9C and 10A-10C, the angle may be set using shape memory metal such as nitinol. A support structure, such as a Kirschner pin is inserted in the channel 86 (96). This effectively straightens the predetermined angle back to an unbent position or configuration. The device 80 (90) is inserted into the bore dimensioned through a first phalange 71 and a bore 74 dimensioned in the proximal end of the adjacent phalange 72. Alternatively, a Kirschner pin may be inserted first into a patient and used as a guide for channel 86 (96) and proper insertion of the device 80 (90). The device, anchored in the phalanges, is oriented using the orientation marking on the second end 85 (95) of the device. Once the desired orientation is achieved, the Kirschner pin is removed the device 80 (90) returns to its previously predetermined bent (angled) configuration and the phalanges are bent into the predetermined angle of the device. A cap of any suitable material may be added to the second end 85 (95) once the Kirschner pin is removed if desired.

The device may be made in different scales for different patient needs, such as sizing for children or adult patients. Having thus described some embodiments of the invention, other variations and embodiments that do not depart from the spirit of the invention will become apparent to those skilled in the art. The scope of the present invention is thus not limited to any particular embodiment. Unless expressly stated otherwise, the steps of any method described herein may be performed in any order capable of yielding the desired result.

What is claimed is:

1. A device for fusing joints in an angle of between 5° and 70° comprising:
    a single shaft comprised of non-biodegradable material and having:
    (i) a first end;
    (ii) a second end; and
    (iii) a middle bendable section;
    (iv) a first section between the first end and the middle bendable section the first section having threads that can be threaded into and retained in a first joint bone; and
    (v) second section between the second end and the middle bendable section the second section having threads that can be threaded into and retained in a second joint bone;
    (vi) a first position wherein the device is essentially straight after being inserted into the first joint bone and second joint bone;
    (vii) a second position wherein the first section is straight, the second section is straight and the middle, bendable section is angled after the device is inserted into the first joint bone and second joint bone and force is applied to bend the middle, bendable section; and
    (viii) a channel to receive a support structure.

2. The device of claim 1 wherein the channel is formed in the center of the device.

3. The device of claim 1 wherein the device includes a support structure inserted in the channel and the device is pre-formed in an angled position of between 10° and 75° and the support structure is removed to initiate movement of the device from the essentially straight position to the pre-formed angled position.

4. The device of claim 3 wherein inserting the support structure into the channel initiates the movement of the device from the angled position to the essentially straight position.

5. The device of claim 1 wherein the channel has an approximately uniform diameter.

6. The device of claim 1 wherein the channel is closed at the first end.

7. The device of claim 1 wherein the channel further comprises an end cover coupled to the second end of the channel configured to prevent access to the channel.

8. The device of claim 1 that is between ½" and 2" long.

9. The device of claim 1 that is between ¾" and ¾" long.

10. The device of claim 1 that is between 1 mm to 5 mm in diameter at its thickest point.

11. The device of claim 1 that is about 3 mm in diameter at its thickest point.

12. The device of claim 1 wherein the threads of the first section have a larger thread outer diameter than the threads of the second section.

13. The device of claim 1 wherein the threads of the second section have the same thread outer diameter as the threads of the first section.

14. The device of claim 1 wherein the first end includes a self-tapping feature.

15. The device of claim 1 wherein the second end includes a head adapted to receive an end of a driving tool.

16. The device of claim 15 wherein the driving tool is a screwdriver.

17. The device of claim 1 wherein the middle bendable section is designed to bend in one direction.

18. The device of claim 1 wherein the middle bendable section is designed to bend in more than one direction.

19. The device of claim 1 wherein the second end includes an orientation marker for aligning the device to determine the location and position of the middle bendable section.

20. The device of claim 1 wherein the device has a length and the middle bendable section comprises between 20% to 75% of the length.

21. The device of claim 1 wherein the device has a length and the middle bendable section comprises between 25% to 50% of the length.

22. The device of claim 1 wherein at least a portion of the middle bendable section has a cross-sectional area that is less than one or more of: the cross sectional area of part of the first section and the cross-sectional area of part of the second section.

23. The device of claim 22 wherein the cross sectional area of the middle bendable section is round.

24. The device of claim 1 wherein between 2 and 30 lbs. of force are required to bend the middle bendable section once the device is implanted into a joint.

25. The device of claim 1 wherein between 2 and 10 lbs. of force are required to bend the bendable section once the device is implanted into a joint.

26. The device of claim 1 wherein the middle bendable section is comprised of the same material as the rest of the device.

27. The device of claim 1 wherein at least part of the middle bendable section comprises a different material than the rest of the device.

28. The device of claim 1 wherein at least part of the first end, second end, and middle bendable section are comprised of nitinol.

29. The device of claim 1 that comprises (a) a flexible tube, (b) a rigid first section in the shape of a collar adhered to the tube near the first end, and (c) a rigid second section in the shape of a collar adhered to the tube near the second end.

* * * * *